(12) United States Patent
Edelson et al.

(10) Patent No.: US 9,404,834 B2
(45) Date of Patent: Aug. 2, 2016

(54) ACTIVE RESISTANCE DYNAMOMETER FOR WHEEL TESTING

(71) Applicant: Borealis Technical Limited, North Plaines, OR (US)

(72) Inventors: Jonathan Sidney Edelson, Portland, OR (US); Scott Perkins, Kent, WA (US); Robert M. Sweet, Beaver, UT (US); Isaiah W. Cox, Baltimore, MD (US)

(73) Assignee: Borealis Technical Limited, Gibraltar (GI)

( * ) Notice: Subject to any disclaimer, the term of this patent is extended or adjusted under 35 U.S.C. 154(b) by 0 days.

(21) Appl. No.: 14/389,362

(22) PCT Filed: Mar. 28, 2013

(86) PCT No.: PCT/US2013/034219
§ 371 (c)(1),
(2) Date: Sep. 29, 2014

(87) PCT Pub. No.: WO2013/148916
PCT Pub. Date: Oct. 3, 2013

(65) Prior Publication Data
US 2015/0040679 A1 Feb. 12, 2015

Related U.S. Application Data

(60) Provisional application No. 61/617,024, filed on Mar. 28, 2012.

(51) Int. Cl.
*G01L 1/22* (2006.01)
*G01M 17/013* (2006.01)
*G01M 17/007* (2006.01)
*G01L 5/26* (2006.01)

(Continued)

(52) U.S. Cl.
CPC ............... *G01M 17/013* (2013.01); *G01L 5/26* (2013.01); *G01L 5/28* (2013.01); *G01M 17/0074* (2013.01); *G01N 3/00* (2013.01)

(58) Field of Classification Search
CPC .. G01L 5/28; G01M 17/0074; G01M 17/013; G01N 3/00
USPC ......................................... 73/862, 146, 865.3
See application file for complete search history.

(56) References Cited

U.S. PATENT DOCUMENTS

| | | | |
|---|---|---|---|
| 3,898,875 A | 8/1975 | Knoop et al. | |
| 3,937,076 A * | 2/1976 | Pommellet | G01M 17/022 73/146 |
| 4,161,116 A * | 7/1979 | Fegraus | G01M 17/0072 73/116.06 |

(Continued)

*Primary Examiner* — Max Noori

(57) ABSTRACT

A wheel testing system and method are provided that simulates realistically conditions likely to be encountered during operation of vehicle wheels, especially powered drive wheels and wheel-connected structures. The system may include an integral support frame designed to adjustably mount wheels or wheel-connected structures to be tested, a load motor drivingly connected to an inertial load, and an adjustable mounting sled configured to adjustably mount a test wheel or a wheel-connected structure with an hydraulic system actuatable to adjust the location of the test wheel relative to the inertial load to vary or fix the load on the test wheel desired. Speed of the test wheel can be varied or fixed by controlling the speed of the load motor. System measurement and data collection electronics measure a range of selected wheel parameters and gather data for transmission to a processor or non-transitory storage medium for processing and evaluation.

19 Claims, 4 Drawing Sheets

(51) Int. Cl.
*G01L 5/28* (2006.01)
*G01N 3/00* (2006.01)

(56) References Cited

U.S. PATENT DOCUMENTS

| | | | |
|---|---|---|---|
| 4,753,110 A | 6/1988 | Burchett et al. | |
| 4,807,467 A | 2/1989 | Kugler | |
| 5,101,660 A * | 4/1992 | La Belle | G01M 17/0072 73/116.06 |
| 5,402,674 A * | 4/1995 | Ganzhorn, Jr. | G01M 17/0074 73/116.06 |
| 5,945,598 A | 8/1999 | Enright | |
| 6,257,054 B1 * | 7/2001 | Rostkowski | G01L 3/22 73/116.08 |
| 6,813,938 B2 * | 11/2004 | Schwendemann | G01M 17/022 73/146 |
| 2010/0251832 A1 * | 10/2010 | Kirkpatrick | G01M 17/0074 73/862.191 |
| 2011/0077892 A1 | 3/2011 | Emami et al. | |

* cited by examiner

ACTIVE RESISTANCE DYNAMOMETER FOR WHEEL TESTING

PRIORITY CLAIM

This application claims priority from U.S. Provisional Application No. 61/617,024, filed Mar. 28, 2012, the disclosure of which is fully incorporated herein.

TECHNICAL FIELD

The present invention relates generally to systems for testing wheels and other rotational structures and specifically to an active resistance dynamometer for testing wheels and wheel-connected or wheel-related structures and functions.

BACKGROUND OF THE INVENTION

Dynamometers have long been used to determine the force, torque, and power produced by rotating machines and other rotating devices and systems of various types for testing, calibration, and similar purposes. Most of these kinds of dynamometers are equipped with some way to measure the operating torque and rotational speed or angular velocity of the unit or system to be tested or evaluated. Power is then calculated from these measurements. Either torque or speed can be maintained constant during operation of the dynamometer while the other parameter of the machine, device, or system being tested is measured. Typically, a dynamometer will include an absorber/driver unit that is rotatably coupled to the machine or system to be tested so that this unit can rotate at whatever speed is required for testing and has structure designed to develop a braking torque. Torque measurement can be made in a variety of ways, including through the use of torque transducers that provide an electrical signal proportional to torque. Speed measurements can also be made similarly through speed sensors or transducers that provide electrical signals proportional to speed. These electrical signals can be transmitted to appropriate processors for analysis.

Some currently available dynamometers use electric motor/generators as absorber/driver units. Either an alternating current (AC) motor or a direct current (DC) motor can operate as a generator that is driven by the machine or device being tested. These dynamometers are equipped with control elements, usually a variable frequency drive for an AC motor or a DC drive for a DC motor. If the control elements are regenerative, power can be transferred from the machine being tested to an appropriate destination.

There are, in addition, various types of dynamometer systems, depending on the type of load applied to the machine or system being tested. For example, a brake type of dynamometer applies a variable load and measures the machine's ability to move or hold speed compared to an applied braking torque and calculates power output from the applied braking torque. An inertia type of dynamometer provides a fixed inertial load with a known mass, usually a heavy drum, and calculates the power required to accelerate that load from recorded speed and acceleration rate of the machine or device to be tested. Torque can be calculated from recorded speed and acceleration rate. These dynamometer systems have real world limitations, however. The use of a fixed inertial load, for example, requires all load tests to be conducted under acceleration conditions. In situations in which a machine or system must also be able to perform under fixed speed conditions, the use of a fixed inertial load cannot determine machine or system performance. Testing a machine, device, or system at a speed that is variably set by a variable load is not possible with the systems described.

A direct motor type of dynamometer, which has two opposing motors and is typically used to test one of the motors, may effectively test the motor, but cannot effectively test other structures, such as, for example, vehicle wheels, load on a wheel due to brakes, and the like. In a vehicle with one or more drive wheels powered by a motor, the ability to test such drive wheels, as well as any associated structures that constitute a load on the wheel, can provide essential performance information. This capability is not provided by currently available dynamometers.

A range of dynamic load test systems has been described in the prior art. In U.S. Pat. No. 3,898,875, for example, Knoop et al describe a system for testing an electric motor that is rigidly mounted in a stationary platform and fixedly coupled through torque and speed transducers to a load motor that is designed to test dynamic characteristics of the motor under test over a short time interval. Linear deceleration is followed by linear acceleration during the testing interval, which is short enough to prevent substantial heating of the test motor. U.S. Pat. No. 4,807,467 to Kugler describes a testing system useful for drive units, including complete motor vehicles, internal combustion engines, transmissions, brake systems, and the like, that provides a realistic simulation of flywheel masses and torque variations. This system, which employs a hydrostatic motor and supporting hydraulic apparatus, is stated to allow precise regulation and adjustment of a desired load and torque more accurately than electric motor equipment used for the same purpose. U.S. Patent Application Publication No. US2011/0077892 to Emamai et al describes a test platform for testing electric motors under specific load conditions to which the motor will be subjected in real-world applications that is designed to enable motor purchasers to connect a motor accurately to the test platform and evaluate the motor prior to purchase. A load emulator also permits components other than motors, such as motor drive systems, transmission mechanisms, including harmonic drives, planetary gear boxes, and the like, and rotary internal combustion engines to be tested. This system additionally enables the testing to be conducted remotely over a network.

The patent art has also proposed dynamometers for testing aircraft components. U.S. Pat. No. 4,753,110 to Burchett et al describes a dynamometer useful for measuring forces, brake torque, and rolling resistance of tires and brakes of aircraft, as well as other vehicles, in which a runway is simulated by the surface of a rotatable drum, and a tire wheel and brake assembly is adjustably mounted on a transducer head connected to a mounting plate that can be adjusted to change the camber and yaw angle of the tire, while a traveling carriage connected to the mounting plate may be advanced toward the drum by a drum ram. In U.S. Pat. No. 5,945,598, Enright describes a dynamometer for testing aircraft brakes that realistically simulates brake and landing gear vibration dynamics, particularly the vibrational coupling between brakes and gear walk, in which a hydraulic pitch motion inducer forces a wheel tire and brake assembly against a road wheel or drum. The load is designed to simulate aircraft weight for an individual wheel and brake assembly. Neither of these patents suggests testing a powered aircraft wheel or wheel connected structures or functions under realistic acceleration and deceleration conditions and fixed and/or variable speeds or loads.

None of the prior art described above suggests an integrated active resistance dynamometer testing apparatus with the capability for testing a wheel or a powered wheel system under simulated realistic load and speed conditions in which either and/or both load and speed can be flexibly varied or fixed to measure desired selected parameters relating to wheel function or operation. The prior art, moreover, also fails to suggest such a testing apparatus that can accommodate and perform such tests on wheels, wheels powered by drivers or motors, brakes or other loads on wheels, tires, antiskid and/or traction control functions, or other wheel-connected structures and functions under simulated realistic conditions. A need for a system and method to conduct such testing under simulated realistic conditions exists.

SUMMARY OF THE INVENTION

It is a primary object of the present invention to overcome the deficiencies of the prior art and to provide an integrated active resistance dynamometer testing system and method for testing wheels, wheel drivers, and a range of wheel-connected or wheel-related components and functions under simulated realistic conditions.

It is another object of the present invention to provide a testing system designed to test a powered vehicle wheel under a range of fixed and variable simulated speed and torque conditions likely to be encountered during actual operation of the powered wheel.

It is an additional object of the present invention to provide an active resistance dynamometer capable of testing wheels and wheel systems under load at a fixed speed and at a speed that is set by a variable load.

It is a further object of the present invention to provide a testing system and method for wheels, wheel drive means, and wheel-connected systems that uses a motor, an inertial load, and a hydraulic system to produce a variable load and set a variable speed.

It is yet another object of the present invention to provide an active resistance dynamometer capable of testing wheel traction control in a powered or non-powered wheel under simulated realistic conditions.

It is yet a further object of the present invention to provide a wheel testing system and method useful for evaluating a powered aircraft drive wheel, the drive means used to power the aircraft drive wheel, the powered wheel tires, brakes, and other wheel-connected structures, and powered wheel traction control under simulated realistic conditions.

In accordance with the aforesaid objects, a wheel testing system and method are provided that simulates realistically conditions likely to be encountered during actual operation of vehicle wheels, especially powered drive wheels and wheel-connected structures. The system of the present invention includes an integral support frame designed to variably mount a range of wheels and wheel-related and wheel-connected structures to be tested, a load motor drivingly connected to an inertial load, and an adjustable mounting sled configured to rotatably and adjustably mount a test wheel and/or a wheel-connected structure with an associated hydraulic system actuatable to adjust the location of the test wheel relative to the inertial load so that the load on the test wheel can be varied as desired. Speed of the test wheel is varied by varying the speed of the load motor. Measurement and data collection electronics are connected to the system to measure a range of selected wheel parameters during the test and gather data, which is preferably transmitted to a processor and/or a non-transitory storage medium for processing and evaluation.

Other objects and advantages will be apparent from the following description, drawings, and claims.

DESCRIPTION OF THE INVENTION

The active resistance dynamometer of the present invention provides a versatile testing and evaluation system for wheels and a range of wheel-connected and wheel-related structures and functions. Unlike available testing and evaluation systems, the present system provides an apparatus and method for testing wheel and wheel-connected structures and functions under simulated conditions that are more realistic than has heretofore been possible. The present system has the capability to vary either and/or both the speed of the wheel or wheel-connected structure under test and the load on the wheel or wheel-connected structure. Consequently, load tests can be done during acceleration or deceleration situations or at a fixed speed. The load on the wheel can be varied while the speed is fixed, and speed can be set by a variable load instead of inertial mass.

Figure 1:
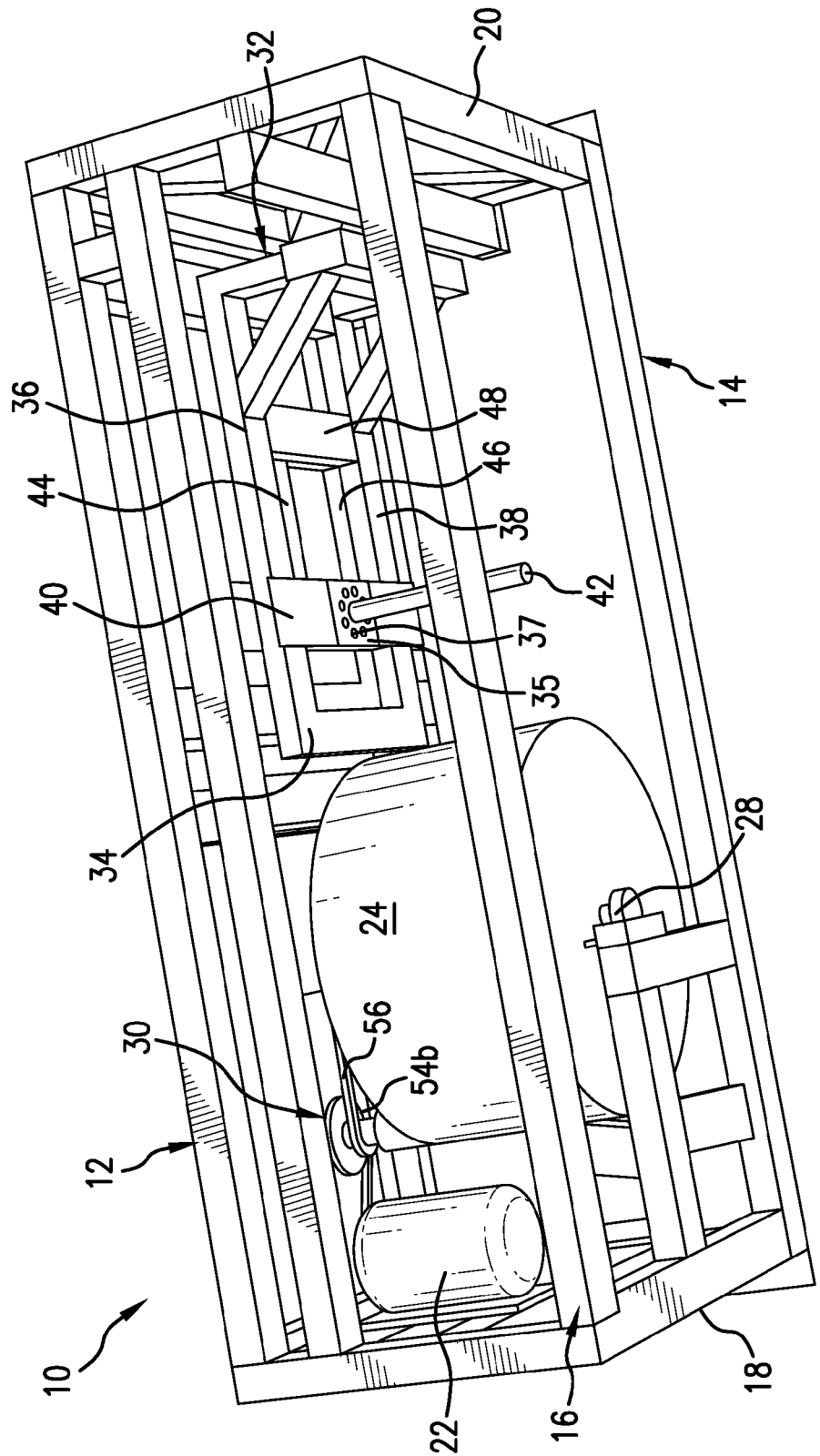
FIG. 1 is a top perspective view of the testing system of the present invention.

Referring to the drawings, FIG. 1 illustrates the active resistance dynamometer 10 of the present invention from a top perspective view. The dynamometer includes a substantially rectangular frame 12 with a base member 14, an opposed top element 16, and opposed side elements 18 and 20 positioned perpendicularly between the base member 14 and the top element 16 to connect the base member 14 and the top element 16. The frame 12 is shown in the drawings in a substantially horizontal orientation with the length of the base member 14 greater than the height of the side elements 18 and 20. The frame could also be oriented vertically. In a vertical orientation, one of the side elements 18 or 20 would serve as a base member contacting a floor or similar surface, and the opposed side element would serve as a top element. The base member 14 and the top element would then form the sides of the frame 12. In a vertical orientation, the height of the frame is significantly greater than the length or side-to-side dimension. In some applications, the horizontal frame orientation may be preferred, while in others, the vertical frame orientation will be preferred. Additional frame elements may be attached to the frame 12 to support components of the dynamometer system, as will be described below. The positions and locations of various components and elements of the present system will be described as shown in the drawings. Other positions and locations in relation to the frame 12 for these components and elements, however, are also contemplated to be within the scope of the present invention. Moreover, the dimensions of the frame 12 may be varied to accommodate wheels and wheel-connected or wheel-related structures or components of a variety of sizes.

FIG. 1 shows the testing components of the present invention. A load motor 22 may be mounted on or adjacent to side element 18. A separate frame mounting element (not shown) may be secured to the side element 18, and the load motor 22 may be mounted to this. The load motor 22 may be any kind of motor capable of driving a load of the size required to conduct the desired wheel tests. An electric motor, which can be either an alternating current (AC) motor or a direct current (DC) motor, is a preferred load motor. Other types of motors, such as, for example hydraulic or pneumatic motors, could also be used.

The load motor 22 is connected to drive an inertial load, which is represented by drum 24, which may be rotatably mounted on an axle (element 26 in FIG. 4), that preferably has a length that is at least the width of the drum. The axle may be fixed to the dynamometer frame by a drum support 28. Adjustment pins, such as those described below in connection with other system components, are preferably provided to permit the some flexibility in positioning the drum 24 with respect to the load motor 22. A drive system 30, preferably formed of a series of gears or a gear train connected by belts, chains, or the like, may drivingly connect the load motor 22 to the drum 26. When the load motor is operating, it drives the gear train in the drive system 30, which, in turn, drives the drum 24, causing the drum to rotate. The speed of the drum 24 may be varied by adjusting the speed of the load motor 22 to vary the speed of a wheel (not shown) contacting the drum 24.

Figure 2:
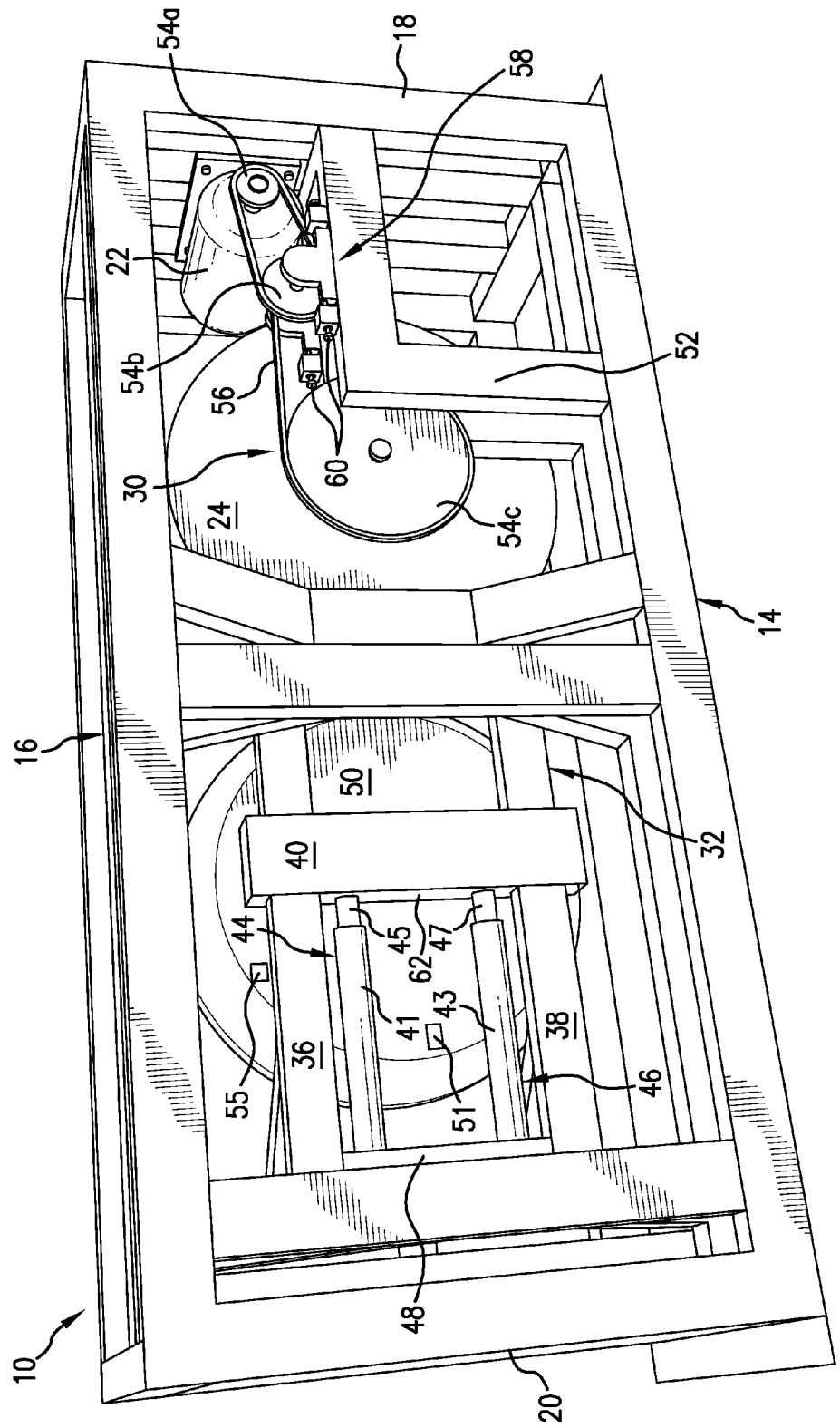
FIG. 2 is a perspective view of one side of the testing system of the present invention with a test wheel mounted on an adjustable mounting sled.
Figure 5:
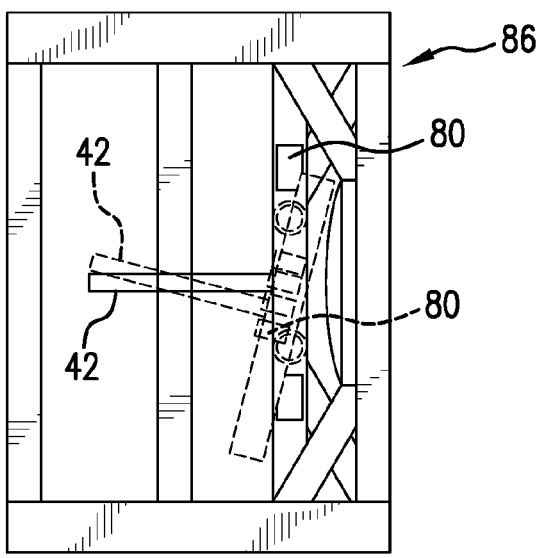
FIG. 5 is an end view of the testing system of the present invention showing the adjustability of the test wheel mounting sled.

An adjustable positionable sled 32, which is designed to hold the wheel or wheel-connected structure to be tested as shown in FIG. 2, may be mounted on the frame 12 between the drum 24 and a dynamometer frame side element 20. The position of the sled 32 can be adjusted from a true vertical position with respect to the frame 12 side element 20, as shown in FIG. 1, to an angled position as shown in FIG. 5. The configuration of the sled 32 shown in FIG. 1 is only one of many possible suitable configurations. The sled 32 has a frame 34, preferably with a substantially rectangular configuration, which facilitates its mounting within the substantially rectangular frame 12. Whatever configuration is used for the sled 32, it should include at least a pair of spaced, substantially parallel rails 36 and 38 for mounting and positioning essential components of the sled.

A wheel mount member 40 may be slidably mounted between the rails 36 and 38 and may be structured to engage rails 36 and 38 to permit linear sliding movement of the wheel mount member 40 toward and away from the drum 24. The wheel mount member 40 may include an axle 42, preferably centrally positioned on the wheel mount member 40, that can rotatably support a wheel and/or a wheel and wheel-connected structures (not shown) to be tested. The axle 42 may include a mounting plate 35 that is mounted on the wheel mount member 40 by suitable mounting pins 37.

A pair of hydraulic pins 44 and 46 may be mounted on the sled, preferably in locations substantially parallel to the sled rails 36 and 38 and perpendicular to the wheel mount member 40, to extend from a hydraulic base plate 48 on the sled to the wheel mount member 40. Suitable hydraulic lines, a source of hydraulic fluid, and a hydraulic actuator for operating the hydraulic pins 42 and 44 (not shown) may be provided. Hydraulic cylinder throw is preferably adjusted by adjustment pins positioned in suitable locations as will be described below.

FIG. 2 is a view of the dynamometer frame 12 from the opposite side shown in FIG. 1 with a wheel 50 mounted in place for testing on the axle 42 on the wheel mount member 40. The drive system 30 can be seen more clearly in this view. A drive system mounting frame 52 may be provided to support the drive system 30. While the rectangular configuration shown in FIG. 2 is a convenient shape, other structures with shapes that operationally support a drive system could also be used. The drive system preferably includes a gear train with a series of rotary drive gears 54a, 54b, and 54c that may drivingly connect the load motor 22 with the drum 24 so that the speed and torque of the load motor may be transferred to the drum. A series of belts 56 may drivingly connect the gears 54a, 54b, and 54c with each other and with the load motor 22 and the drum 24. As previously indicated, chains or other suitable devices may also be used for this purpose. The position of the drive system 30 on the frame 52 relative to the load motor 22 and the drum 24 can be adjusted. A gear mount 58 with a plurality of adjustment pins 60 may be provided on the drive system mounting frame 52 for this purpose. Other drive system supports and gear mounts that perform this function are also contemplated to be within the scope of the present invention. The type of drive system employed may determine the type of drive system support selected.

The structural and functional relationship of the wheel mount member 40 and the hydraulic pins 44 and 46 can be seen in the FIG. 2 view of the present dynamometer. The hydraulic pins 44 and 46 may be located within the framework of the adjustable, movable sled 34 between the rails 36 and 38 to extend from a base plate 48 to connect with the wheel mount member 40 at hydraulic pin connector 62. The hydraulic pin connector 62, which is preferably secured to the wheel mount element 40, may be integrally or removably connected to both hydraulic pins 44 and 46 as shown in FIG. 2. Each hydraulic pin 44 and 46 may include a respective outer cylinder 41 and 43 with a respective movable piston 45 and 47 disposed within each cylinder. The pistons are the portions of the hydraulic pins 44 and 46 that are actually connected to the hydraulic pin connector. The extent of linear movement of the wheel mount member 40 may be limited by the length of the pistons 45 and 47, although this can be changed, as shown and discussed in connection with FIG. 3. Hydraulic fluid supplied to each cylinder 41 and 43 will push the respective pistons 45 and 47 in the direction of the drum 24, causing the connected wheel mount member 40 and the wheel 50 to move toward the drum 24, increasing the load on the wheel 50. Removal of hydraulic fluid from the cylinders 41, 43 will have the opposite effect, and the pistons 45, 47 will retract into the cylinders, pulling the wheel mount element 40 away from the drum 24. Controlling the position of the hydraulic pin pistons 45 and 47 effectively controls the load on the test wheel 50. Any type of hydraulic system capable of moving pistons within cylinders as discussed can be employed for this purpose.

Figure 3:
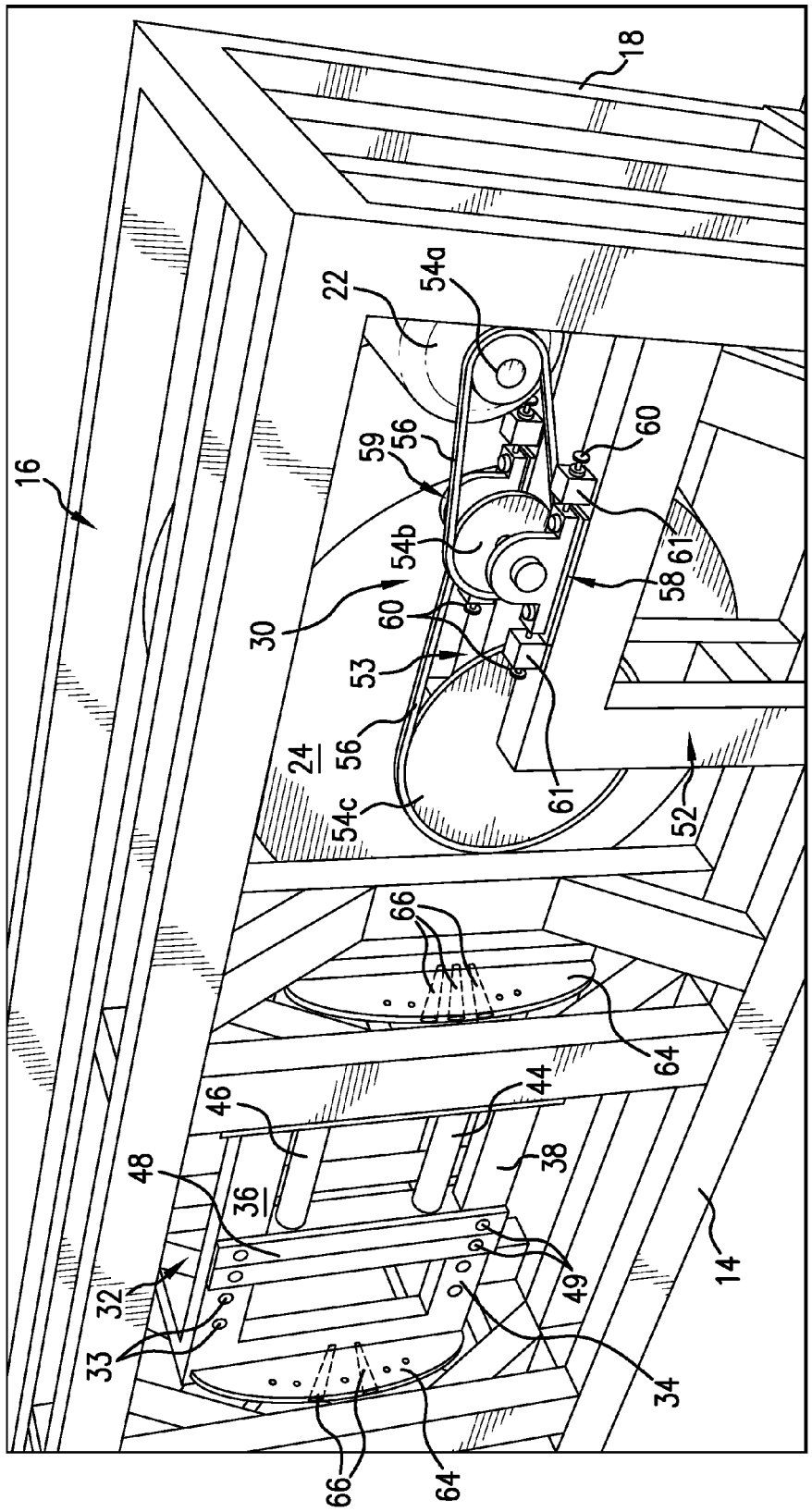
FIG. 3 is a perspective view of a portion of the side of the testing system of the present invention shown in FIG. 2.

FIG. 3 shows a view of the dynamometer of the present invention from the same side as in FIG. 2, but from a slightly different perspective. In the FIG. 3 perspective, the drive system 30 supports and connections are shown more clearly. Gear 54a may be mounted on the load motor 22 and may be connected by a belt 56 or the like to a central gear 54b, which may be connected by a belt 56 or the like to a gear 54c associated with the drum 24. Other numbers of gears besides the three shown may be more appropriate in some applications and could be used. The gear mount 58 may be located on the drive system mounting frame 52, preferably adjacent to gear 54b, but could also be located in another convenient location. A second drive system mounting frame 53, which may be substantially similar to and spaced inwardly of the drive system mounting frame 52, can be seen in FIG. 3. Gears 54b and 54c may be rotationally mounted in the space between the two drive system mounting frames. Gear mount 58 may have a corresponding gear mount 59 on drive system mounting frame 53, and the two gear mounts may rotationally support gear 54b. Adjustment pins 60 and adjustment pin blocks 61 on both drive system mounting frames 52 and 53 may allow adjustment of the position of gear 54b relative to gears 54a and 54c.

The positionable sled 32 may be designed so that its position can be tilted or otherwise changed to adjust the position of the wheel 50 or whatever wheel-connected or related structure or function is being tested. For example, the camber or angle of rotation of the wheel relative to the drum 24 can be changed by adjusting the sled position. The linear travel of the sled 32 is not affected by adjusting the tilt of the sled. As shown in FIG. 3, the sled 32 may include opposed curved extensions 64 at opposite ends of sled frame 34 that extend perpendicularly between the rails 36 and 38 toward the dynamometer frame. Adjustment shims 66 can be provided to hold the sled 32 in a desired tilted position relative to the drum 24 surface. The hydraulic base plate 48 may also be adjustable. Adjustment pins 49 may removably engage corresponding pin holes 33 in sled rails 36 and 38. Movement of the hydraulic base plate 48 toward or away from the drum 24 can change the effective length of the pistons 45 and 47.

Figure 4:
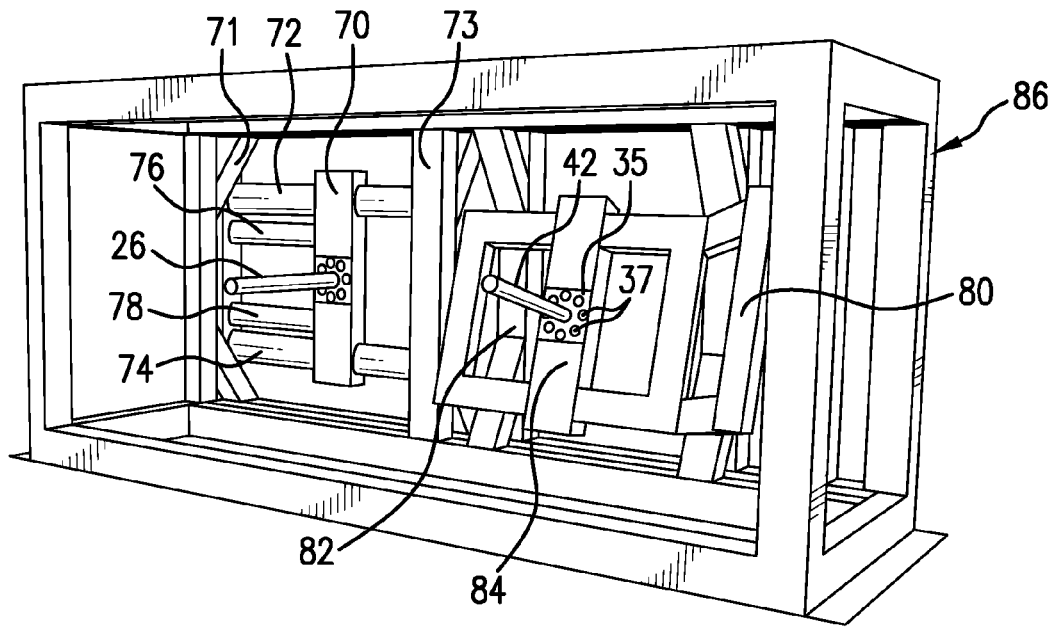
FIG. 4 is a perspective view of the testing system of the present invention from a side opposite to that shown in FIG. 2 with the load motor, drive system, and inertial load removed.

FIG. 4 shows the dynamometer of the present invention from the same view as in FIG. 1. In the FIG. 4 view, however, the operational elements, including the load motor 22, the drum 24, and the drive system 30 have been removed. This view also demonstrates the versatility of the present dynamometer design. The axle 26, which held the drum 24 in FIGS. 1-3, may be located on a mount element 70 slidably mounted between rails 72 and 74 attached to dynamometer frame elements 71 and 73. A pair of hydraulic pins 76 and 78 may be mounted substantially parallel to rails 72 and 74 to move the mount element 70 linearly along the rails 72 and 74. A drum, such as drum 24, or a load motor, such as motor 22, could be mounted on axle 26 on the mount element 70. The drum, load motor, or other element may then move in response to the action of pistons (not shown) in the hydraulic pins 76 and 78 as described above in connection with FIGS. 2 and 3.

A tiltable, adjustable sled 80 may be supported within the dynamometer frame at a desired angle with respect to the frame. Curved frame mounts 82, only one of which is clearly visible in FIG. 4, which are functionally similar to the curved sled extensions 64 in FIG. 3, can be provided to adjust the angle of the sled. When a wheel is mounted on the sled, the camber or angle can be changed by the tilt of the sled 80. The axle 42, used to mount a wheel or wheel-connected structure for testing, may be secured by a base plate 35 and pins 37 to an axle support 84. The location of the axle support 84 can be fixed on the sled 80. Alternatively, axle support 84 can be mounted for linear movement on the sled frame, as described above, to provide maximum adjustability of the position of the wheel during testing.

FIG. 5 is a view of the dynamometer of FIG. 4 from the end 86 adjacent to the tiltable sled 80. FIG. 5 shows two different positions, A and B, of the sled 80. In position A, shown in solid lines, the sled 80 is substantially parallel to the frame 86, and the axle 42 is perpendicular to the frame 86. In position B, shown in dashed lines, the sled 80 is tiled at an angle with respect to the frame 86, and the axle 42 is tilted upwardly of the position it occupied in position A. The degree of tilt may depend, in part, on which wheel structures and/or functions are being tested.

Reference will be made to the dynamometer arrangement shown in FIGS. 1-3 in discussing the operation of the dynamometer to test vehicle wheels, wheel-connected structures, and wheel-related functions. The alternative arrangement of FIGS. 4 and 5 may function in substantially the same way. As shown in FIG. 2, a load motor 22 may be connected to the dynamometer, a drum 24 may be mounted on an axle 26, and a drive system 30 with gears or another suitable drive means may be mounted on the dynamometer to provide a driving connection between the load motor and the drum. Although a motor is preferred to provide a load in connection with a drum, any suitable device capable of providing a fixed and a variable load may be used in the present testing system. The drum 24 could be any suitable type of rotating inertial load or functionally similar device. The hydraulic pins used to move the movable wheel mount member 40 or the axle support 70 can be actuated by a range of available hydraulic systems.

A wheel 50 to be tested may be mounted on the axle 42 on the sled 32. The sled 32 may be positioned so that the angle of the wheel 50 relative to the drum 24 is set as desired. The dynamometer system may be connected to measurement electronics (not shown) to measure selected desired parameters of wheel function. The measurement electronics should be capable of measuring at least power, current, voltage, frequency, torque, and speed, as well as any other desired parameters. Transducers, sensors, and the like, such as transducer 51 and sensor 55, are preferably provided on the wheel 50, as shown, or on another wheel-connected structure to be tested to obtain required information relating to these and other selected parameters during testing. Control electronics may be provided. Suitable processors, non-transitory storage media, and the like are also preferably provided to facilitate data collection, processing, and evaluation during and/or after testing.

When a wheel is mounted for testing, the dynamometer system load motor 22 may be activated and driven, preferably by an inverter, but other drivers could be used, causing the drum 24 to be driven by the drive system 30. Actuation of the hydraulic pins 44 and 46 on the sled 32 may extend the pistons 45 and 47 from their respective cylinders 41 and 43 and cause the wheel mount 40 to slide along the rails 36 and 38 of the sled to move the wheel toward and into contact with the rotating drum 24. Contact between the wheel 50 and the drum 24 can be varied by actuating and de-actuating a hydraulic system (not shown) connected to the hydraulic pins to extend and retract the pistons, thereby moving the wheel 50 into stronger contact with the drum 24 or into lighter or no contact with the drum 24. The speed of rotation of the drum 24 is transferred to the wheel 50 being tested. Control of the speed of rotation of the drum 24, either through the load motor 22 or the drive system 30, can vary the wheel speed. Either or both of the load on the wheel and the speed can, therefore, be varied over a very wide range of possible combinations of loads and/or speeds that more realistically simulate actual load and speed conditions. This heretofore has not been possible with available dynamometers or like testing apparatus.

Since the drum 24 may be mechanically connected to a load, the drum resistance operates in the system shown and described herein as a generator. Power generated during testing can be put back into the system, can be sent to the power grid, or can be used for any other purpose.

While the term wheel has been used herein, and this term is intended to refer to any vehicle wheel, the present dynamometer system is especially effective for testing powered or driven vehicle wheels. Such wheels are typically powered or driven by electric or other motors, and the testing system described above can provide valuable information about the wheel motor as well as tires mounted on powered wheels and brakes connected to powered wheels. Additionally, information related to traction control and antiskid functions of powered and non-powered wheels can be obtained by the present system. One application of the present system includes the testing of driven wheels or wheels powered by onboard non-engine drive means designed to drive aircraft autonomously on the ground during taxi. The testing capability of the present invention can help to ensure the optimum performance of aircraft and other vehicle wheels, as well as wheel-connected structures and wheel-related functions.

While the present invention has been described with respect to preferred embodiments, this is not intended to be limiting, and other arrangements and structures that perform the required functions are contemplated to be within the scope of the present invention.

INDUSTRIAL APPLICABILITY

The present invention will find its primary applicability as a superior testing system for desired operating parameters for powered and non-powered vehicle wheels under simulated realistic conditions over a wide range of load and speed conditions, wherein either or both of load and speed can be varied to optimize measurement of the desired operating parameters.

The invention claimed is:

1. An adjustable active resistance dynamometer system for testing selected functional and operational parameters of vehicle wheels and wheel-connected or wheel-related structures and functions comprising:
   a. an adjustably positionable sled with adjustable linearly movable mounting structures supporting a vehicle wheel, a wheel-connected structure, or a wheel-related structure in a selected test position;
   b. a rotating variable load application element positioned to apply a fixed or variable load to said vehicle wheel, said wheel-connected structure, or said wheel-related structure in said selected test position;
   c. a variable drive load motor in fixed or variable speed driving relationship with said rotating variable load application element, wherein either or both of the rotating variable load application element and the variable drive load motor is actuatable to vary load and speed as required to test selected functional and operational parameters of said vehicle wheel, said wheel-connected structure, or said wheel-related structure; and
   d. a rectangular support frame positionable in a horizontal or a vertical orientation with a base member in contact with a supporting surface to operationally mount said adjustable positionable sled supporting said vehicle wheel, said wheel-connected structure, or said wheel-related structure, said rotating variable load application element, and said variable drive load motor within said support frame.

2. The system of claim 1, wherein said adjustably positionable sled is adjustably mounted within said support frame to slide linearly a selected distance along a longitudinal axis of said support frame to move said vehicle wheel, said wheel-connected structure, or said wheel-related structure into and out of operational contact with said rotating variable load application element.

3. The system of claim 1, further comprising an adjustable wheel mounting member slidably mounted on said adjustably positionable sled and hydraulic positioning pins in operational contact with said wheel mounting member and actuatable to move said wheel mounting member into and out of fixed or varying load contact with said rotating variable load application element.

4. The system of claim 1, wherein said rotating variable load application element comprises an inertial load with a drum configuration.

5. The system of claim 1, further comprising a geared drive system interposed between and drivingly connecting said variable drive load motor and said rotating variable load application element.

6. The system of claim 5, wherein said geared drive system comprises a gear train mounted on said support frame and adjustably positioned between said variable drive load motor and said rotating variable load application element.

7. The system of claim 1, further comprising electronic measurement elements positioned in measuring contact with said vehicle wheel, said wheel-connected structure, or said wheel-related structure to obtain desired selected measurements relating to selected functional or operational parameters of said vehicle wheel, said wheel-connected structure, or said wheel-related structure.

8. The system of claim 7, wherein said desired selected measurements relate to one or more selected operational or functional parameters comprising power, current, voltage, frequency, torque, and speed.

9. The system of claim 1, wherein said vehicle wheel comprises a motor-powered drive wheel.

10. The system of claim 9, wherein the vehicle is an aircraft and said motor-powered drive wheel comprises an aircraft landing gear wheel powered by an onboard electric drive motor.

11. The system of claim 7, wherein said selected functional or operational parameters relate to traction control.

12. The system of claim 1, further comprising an adjustably positionable load mounting member supporting said rotating variable load application element slidably mounted within said support frame and adjustably positioned by hydraulic positioning pins in operational contact with said load mounting member and actuatable to move said load mounting member into and out of load contact with said vehicle wheel, said wheel-connected structure, or said wheel-related structure adjustably mounted on said adjustably positionable sled.

13. The system of claim 1, wherein said adjustably positionable sled comprises a tiltable planar sled with a rectangular configuration or a tiltable curved sled adjustably movable to adjust the position of said vehicle wheel, said wheel-connected structure, or said wheel-related structure angularly or linearly with respect to a horizontal or vertical axis of said support frame.

14. A method for testing selected functional or operational parameters of a vehicle drive wheel powered by a drive motor or a component of the vehicle drive wheel, comprising:
   a. providing, within an integral rectangular mounting frame orientable in a horizontal or vertical orientation, an adjustably positionable sled and adjustably mounting a vehicle drive wheel powered by a drive motor to be tested on said adjustably positionable sled;
   b. mounting an actuatable rotating variable inertial load application element comprising a drum, mounting a load motor, and mounting a drive system drivingly connecting the load motor to the drum within said integral rectangular mounting frame;
   c. activating the load motor to actuate the drum through the drive system to rotate the drum at a fixed or variable speed;
   d. moving the adjustably positionable sled with the mounted vehicle drive wheel to be tested into a selected test position so that the vehicle drive wheel is in load applying contact with the drum and causing the vehicle drive wheel to rotate at the fixed or variable speed; and
   e. further actuating either or both of the variable load application element and the drive system to vary load and speed as required to test selected functional and operational parameters of the vehicle drive wheel.

15. The method of claim 14, further comprising operating said actuatable rotating variable inertial load application element as a generator, and returning power generated when said vehicle drive wheel is in load applying contact with said actuatable rotating variable inertial load application element and the generated power is available to be used to practice said method.

16. The system of claim 1, further comprising, when said rectangular support frame is positioned in said horizontal orientation, said adjustable positionable sled, said rotating variable load application element, and said variable drive load motor are operationally supported within said rectangular support frame along a longest horizontal axis of said rectangular support frame.

17. The system of claim 5, further comprising a plurality of adjustment pins on each of said adjustably positionable sled, said rotating variable load application element, said variable drive load motor, and said drive system and a corresponding plurality of adjustment pin receptacles on said support frame to adjustably support positions of one or more of said adjustably positionable sled, said rotating variable load application element, said variable drive load motor, and said drive system within said support frame.

18. The method of claim 14, further comprising mounting an aircraft wheel and a wheel drive motor operational to power said aircraft wheel on said adjustably positionable sled, activating the load motor to actuate the drum to apply a selected load to said aircraft wheel and said wheel drive motor at the fixed or variable speed to simulate conditions during actual operation of said aircraft wheel and said wheel drive motor to move said aircraft, and measuring said selected operating parameters while said selected load is applied to said aircraft wheel and said wheel drive motor.

19. The method of claim 14, further comprising providing measurement electronics, obtaining data from testing said selected functional and operational parameters of the vehicle drive wheel relating to at least power, current, voltage, frequency, torque, and speed, and collecting and evaluating the obtained data.

* * * * *